United States Patent
Goralczyk et al.

(10) Patent No.: US 9,393,190 B2
(45) Date of Patent: Jul. 19, 2016

(54) METHODS FOR ENHANCING SKIN TAN AND REDUCING RISKS OF UV SKIN DAMAGE

(75) Inventors: Regina Goralczyk, Grenzach-Wyhlen (DE); Remo Graeub, Bern (CH)

(73) Assignee: DSM IP ASSETS B.V., Heerlen (NL)

( * ) Notice: Subject to any disclaimer, the term of this patent is extended or adjusted under 35 U.S.C. 154(b) by 353 days.

(21) Appl. No.: 13/037,588

(22) Filed: Mar. 1, 2011

(65) Prior Publication Data

US 2012/0021088 A1 Jan. 26, 2012

Related U.S. Application Data

(63) Continuation-in-part of application No. PCT/EP2010/060487, filed on Jul. 21, 2010.

(30) Foreign Application Priority Data

Jul. 21, 2009 (EP) .................................... 09166022

(51) Int. Cl.

| *A61K 8/97* | (2006.01) |
| *A61K 36/28* | (2006.01) |
| *A23L 1/30* | (2006.01) |
| *A61K 8/36* | (2006.01) |
| *A61Q 5/00* | (2006.01) |
| *A61Q 7/00* | (2006.01) |

(52) U.S. Cl.
CPC ................ *A61K 8/97* (2013.01); *A23L 1/3002* (2013.01); *A61K 8/36* (2013.01); *A61K 36/28* (2013.01); *A61Q 5/00* (2013.01); *A61Q 7/00* (2013.01)

(58) Field of Classification Search
CPC .................................................. A61K 36/185
See application file for complete search history.

(56) References Cited

U.S. PATENT DOCUMENTS

2003/0060428 A1 * 3/2003 Hermansen et al. ............ 514/33

FOREIGN PATENT DOCUMENTS

| EP | 565785 A1 * | 10/1993 |
| EP | 925790 A1 * | 6/1999 |
| EP | 1 666 036 | 6/2006 |
| EP | 1 673 986 | 6/2006 |
| JP | 2-261359 | 10/1990 |
| JP | 3-177386 | 8/1991 |
| JP | 8-325156 | 12/1996 |
| JP | 09052829 A * | 2/1997 |
| JP | 2630798 | 4/1997 |
| JP | 2640603 | 5/1997 |
| JP | 11-193219 | 7/1999 |
| JP | 2006-45170 | 2/2006 |
| JP | 2006174844 A * | 7/2006 |
| WO | 01/58414 | 8/2001 |
| WO | WO2005/027904 | 3/2005 |

OTHER PUBLICATIONS

Pendergast, WR. Publication Date: Oct. 21, 1991 [Retrieved from the Internet on: May 4, 2013]. Retrieved from the Internet: <URL: http://www.holisticmed.com/sweet/stv-petition.txt>.*
International Search Report for PCT/EP2010/060487, dated Sep. 16, 2010.
JP Office Action dated Jun. 2, 2015.
JP Office Action dated Sep. 2, 2014.

* cited by examiner

*Primary Examiner* — Amy L Clark
(74) *Attorney, Agent, or Firm* — Nixon & Vanderhye P.C.

(57) ABSTRACT

The invention relates to the use of an oral composition comprising steviol, a steviol precursors or *Stevia* extract as skin tanning agent. It further relates methods of enhancing the natural skin tan by oral administration of an effective amount of Steviol, a Steviol precursor or *Stevia* extract.

5 Claims, No Drawings

METHODS FOR ENHANCING SKIN TAN AND REDUCING RISKS OF UV SKIN DAMAGE

CROSS-REFERENCE

This application is a continuation-in-part of International Application No. PCT/EP2010/060487, filed 21 Jul. 2010, claiming priority to EP 091660225 filed 21 Jul. 2009, the entire contents of which are hereby incorporated by reference in this application

FIELD OF THE INVENTION

The invention relates to the use of an oral composition comprising steviol, a steviol precursors or *Stevia* extract as skin tanning agent. It further relates methods of enhancing the natural skin tan by oral administration of an effective amount of Steviol, a Steviol precursor or *Stevia* extract.

BACKGROUND OF THE INVENTION

*Stevia rebaudiana* is a plant which is known to contain sweet tasting compounds, including stevioside and rebaudioside A. These compounds are currently being used as sugar substitutes in a number of foodstuffs, including soft drinks. A detailed report regarding their safety, toxicology and metabolism may be found in *Food and Chemical Toxicology* 2008 Vol. 46(7), Supplement 1, where the entire supplement is devoted to rebaudioside A as used in food and beverages. Stevioside and rebaudioside A are metabolized by the mammalian intestinal tract into the aglycone steviol, a compound which is not sweet.

Today, it is important to look healthy and a tanned skin is always a sign of good health. One method of obtaining a tan is to expose skin to UV radiation causing direct DNA damage to the skin, which the body naturally combats and seeks to repair. In the process of repairing the damage and protect the skin, the body creates and releases the brown-colored pigment called melanin into the skin's cells, which gives the skin a darker tone. Melanin is produced by cells called melanocytes and protects the body from direct and indirect DNA damage by absorbing an excess of solar radiation. However, as exposure to UV radiation may have detrimental health effects such as sunburn or even skin cancer many people prefer alternatives which can produce a tanning result without exposure to ultraviolet radiation.

Numerous efforts have been made to identify drugs or other biomolecules that can be orally ingested and that will safely accomplish either or both of the following: (i) cause a tanning (also referred to as darkening of the color/tint/tone; pigmentation; or similar terms) of the skin, in a manner that looks like a healthy and natural suntan, while reducing or eliminating the need to spend hours in direct sunlight or in front of ultraviolet lamps; and/or, (ii) reduce the risk of a sunburn.

However, as the current products used for oral tanning do not deliver satisfactory results there is an ongoing need in the art for compositions which can enhance the natural tan of skin by stimulating the intrinsic melanin formation of a human being and which can be orally ingested.

BRIEF DESCRIPTION OF THE INVENTION

It has been found, in accordance with this invention, that the consumption of an oral composition comprising steviol, a steviol precursor (steviol glycoside), or a *Stevia* extract, preferably one which contains stevioside and/or rebaudioside A (both of which are metabolized physiologically into steviol by the mammalian intestinal tract), has the surprising benefit of activating the melanin formation in human skin melanocytes and can thus be used for sunless skin tanning. Furthermore, the change in pigmentation (i.e. increased melanin content) will render the skin better-prepared to deal with direct sunlight, thereby reducing the risk and/or severity of skin problems such as sunburns, premature wrinkling and aging, skin cancer, etc.

Thus, one embodiment of this invention is a method of enhancing the natural tan of an animal's including human's skin comprising administering an oral composition comprising steviol, a steviol precursor, such as a steviol glycoside, or a *Stevia* extract which contains stevioside and/or rebaudioside A for a time sufficient and in an amount effective to enhance the skin tan, and observing or appreciating the result.

Another embodiment of this invention is the use of steviol, a steviol precursor such as a steviol glycoside, or a *Stevia* extract which contains stevioside and/or rebaudioside A in the manufacture of an oral composition for the enhancement of the natural skin tan.

In a further embodiment the invention relates to a method of reducing the risk of skin damage due to ultraviolet radiation, comprising the step of periodically or intermittently ingesting steviol, a steviol precursor, such as a steviol glycoside, or a *Stevia* extract which contains stevioside and/or rebaudioside A in a quantity and over a span of time sufficient to cause a measurable increase in a person's ability to withstand a fixed dosage of ultraviolet radiation without suffering erythema.

Due to the increased skin pigmentation the skin of animals including humans ingesting steviol, a steviol precursor, such as a steviol glycoside, or a *Stevia* extract which contains stevioside and/or rebaudioside A is better protected against skin damages due to ultraviolet radiation. Thus, another aspect of this invention comprises a method of Preventing or reducing the risk of sun burns, Delaying the onset or severity of photoageing, Preventing or reducing immune suppression Enhancing the photoprotection to both UV A and UV B induced skin damage said method comprising administering an oral composition comprising steviol, a steviol precursor, or a *Stevia* extract which contains stevioside and/or rebaudioside A. In yet another aspect of this invention, steviol, a steviol precursor, or a *Stevia* extract which contains stevioside and/or rebaudioside A is used in a cosmetic oral nutraceutical or food composition for the above advantages involving skin tanning.

Furthermore, the oral composition comprising steviol, a steviol precursor such as a steviol glycoside, or a *Stevia* extract which contains stevioside and/or rebaudioside A can also provide preventive or therapeutic benefits among at least some patients who suffer from, or who are at elevated risk of, various other types of skin conditions, syndromes, or diseases. This includes patients who suffer from albinism, porphyria, or skin blotching or other lesions, and among patients taking certain types of antibiotics that increase their sensitivity to sunlight. Thus, the invention also relates to a method of preventing photosensitivity in people with inherited erythropoietic protoporphyria and/or treatment of vitiligo said method comprising administering an oral composition comprising steviol, a steviol precursor, or a *Stevia* extract which contains stevioside and/or rebaudioside A.

The oral compositions according to the invention are especially attractive, since many people, have a special interest in cosmetic treatments considered as "natural" with mild effects and without major side effects. As orally available compounds, *Stevia* extract and steviol have further advantages in that they are easy to use, do not leave any residue on the skin, and dosages are easier to control than in topical formulations.

*Stevia* extract which contains stevioside and/or rebaudioside A, as used in this invention, may be produced using known methods. This invention is specifically not intended to include the use of *Stevia* extract as a sweetening agent for compositions where an ingredient other than *Stevia* extract, stevioside, rebaudioside A and/or rebaudioside is used to promote the enhancement of the skin tan. Further, the *Stevia* extract of this invention does not contain a bioactive amount of chromenes which is in an amount sufficient to impart a hair growth promoting activity.

Steviol may be obtained by enzymatic hydrolysis of stevioside according to methods described in the literature. Alternatively, since steviol glycosides, such as stevioside and rebaudioside A, are metabolized by the mammalian intestinal tract into steviol, a plant extract containing rebaudiosides and/or steviosides can be used. Preferably, the amount of steviol glycosides is high (>50%). However, these compositions have a very sweet flavor and an aftertaste, so if used in foodstuffs, it is desirable to add a taste masking or taste-enhancing substance.

As an alternative to a plant extract, compositions containing the active ingredients stevioside or rebaudioside A may also be used. Alternatively, and in particular if the skin tanning active compound is to be supplied with food and a sweet taste is not wanted, compositions containing steviol may be used. In all embodiments of the present invention steviol is particularly preferred.

In all embodiments preferably the oral composition is a nutraceutical composition further comprising a nutraceutically acceptable carrier. Furthermore in all embodiments the animal is a human.

DEFINITIONS

The term "skin" means both skin of a human and of an animal.

The term "skin tanning agent" refers to agents who result in or support a darkening of the skin color which may be the result of an increased skin pigmentation (by an increased melanin formation) or other means (e.g. coloration of the skin by a pigment).

The term "oral composition" comprises any composition which is suitable for oral administration.

The term "nutraceutical composition" as used herein includes food products, foodstuffs, dietary supplements, nutritional supplements or a supplement composition for a food product or a foodstuff, including beverages (e.g., but not limited to, sports beverages, functional waters, juices, smoothies; instant drinks), soups, dairy products (e.g., but not limited to, single shot yogurt drinks), nutritional bars, and spreads.

As used herein, the term "food product" refers to any food or feed suitable for consumption by humans or animals.

The term "dietary supplement" refers to a small amount of a compound for supplementation of a human or animal diet packaged in single or multiple dose units. Dietary supplements do not generally provide significant amounts of calories but may contain other micronutrients (e.g. vitamins or minerals).

The term "nutritional supplement" refers to a composition comprising a dietary supplement in combination with a source of calories. In some embodiments, nutritional supplements are meal replacements or supplements (e.g. nutrient or energy bars or nutrient beverages or concentrates).

"Preventing" as used herein is not intended to mean that the event will never occur, but means delaying the onset of the condition or event, and lessening the severity of the condition or event when it does occur.

"Chronic administration" is meant to convey that administration of the active ingredient regularly occurs over an extended period of time, for example once or twice per day for a time of at least about two weeks, preferably for at least one month, and more preferably at least two months. Alternatively, the regular administration can be every two days, every three days, or once per week or twice per week.

"Extended period of time" means substantially daily for a period of time of at least about two weeks, preferably at least about a month, and even more preferably for at least about two months.

"Steviol precursor" means a steviol glycoside that can be enzymatically hydrolyzed to the free aglycone steviol. See, e.g. EFSA Journal 2010, 8(4): 1537, which is hereby incorporated by reference. Enzymes suitable for this hydrolysis are present in certain microbial organisms, also present in the human or animal intestinal tract. See, e.g. Gardana et al 2003 *J. Agric. Food Chem.* 51:6618-22, which is hereby incorporated by reference.

"*Stevia* extract" as used throughout this specification and claims, it is to be understood that the extract is used as an active skin tanning ingredient. Thus, it is either present as the sole active skin tan enhancing ingredient, or if used in combination with another ingredient, its purpose is not that of a sweetener, and/or the amount of the *Stevia* extract is not the amount known to be used for the purpose of sweetening a composition or foodstuff, nor does it contain chromenes in an amount where they have hair growth promoting bioactivity.

"Observing" or "appreciating" may be done by either the individual who ingests the active ingredient, or may be done by a third party. The post-administration condition may be compared with the pre-administration condition and analyzed either using a standard test, or by subjective analysis.

Skin Tanning

More particularly, the present invention relates to the use of oral steviol or steviol-precursor-containing compositions in skin care, particularly for tanning of the skin. It also relates to orally administered skin care compositions, particularly for the tanning of the skin comprising a *Stevia* extract or steviol or steviol precursor and a carrier conventionally used for oral compositions, with the proviso that if present in combination with a second active ingredient, the *Stevia* extract is not present in an amount suitable for the purpose of sweetening the composition. Furthermore, the invention relates to a method of tanning the skin which comprises administering orally to a mammal, in particular a human, in need of such treatment a composition comprising an effective amount of *Stevia* extract, steviol, or steviol precursor and observing the skin tan with the proviso that if present in combination with a second active ingredient, the *Stevia* extract is not present for the purpose of sweetening the composition. For these methods and uses steviol is especially preferred.

Another aspect of this invention is a supplement especially designed for skin tanning and/or sun protection which comprises *Stevia* extract, steviol, or steviol precursor. The humans should eat this supplement daily for at least one month, and preferably for at least two months prior to the sun exposure in order for its skin to be optimal tanned. In preferred embodiments, the supplement is in the form of a tablet or a capsule.

In addition, steviol, a steviol precursor, such as a steviol glycoside, or a *Stevia* extract which contains stevioside and/or rebaudioside A such as particularly steviol can be combined with any other known or hereafter-discovered active ingredients that are believed to be helpful in inducing a skin-darkening response when ingested orally. Such skin tanning agents might include, as examples, carotenoids such as lutein, lycopene, astaxanthin, canthaxanthin, zeaxanthin or beta-carotene as well as melanocyte-stimulating hormones and analogs or active portions thereof, tyrosine such as particularly L-tyrosine, copper, vitamin E and D and/or any or all of the ingredients listed in U.S. Pat. No. 6,254,898 (Bragaglia 2001), which include green tea extract, lipoic acid, and selenomethionine.

Particularly preferred according to the invention is the use of steviol, a steviol precursors or *Stevia* extract which contains stevioside and/or rebaudioside A such as particularly steviol in combination with at least one further agent selected from the group of beta-carotene, lycopene, lutein, L-tyrosine and/or canthaxanthin, vitamin E, vitamin D and copper.

The additional agent is preferably used in effective dosage levels of 0.50-250 mg/day such as 1.0 to 180 mg/day in order to effectively support the darkening of the skin color.

Veterinary Uses

In another aspect of this invention, the *Stevia* extract is administered to a non-human animal, which is preferably a mammal. Since the skin benefits from this invention, the benefits of this invention are not limited to mammals, and may be extended to other animals such as birds, or fish, or other animals where an increased skin coloration is of interest. For example, the bird may be poultry, especially ones which are entered in show competitions. Fish, for example koi and the like, can also benefit from enhanced coloration.

In a preferred aspect of this invention, the non-human animal is a mammal, such as a companion animal (dog, cat, ferret) or an animal which is shown in competition (such as dogs, horses, cats, rabbits and other farm animals). Supplementing the animal's diet with the *Stevia* extract, steviol, or steviol precursor-containing compositions of this invention will enhance the tan of the animal's skin. Thus another aspect of this invention is a veterinary nutraceutical or foodstuff containing a skin tan-enhancing amount of *Stevia* extract, steviol or steviol precursor.

As some animals may not like the taste of the sweet *Stevia* extract, for veterinary uses, it may be preferred that the extract contains steviol rather than a steviol precursor, as steviol does not have a distinctive taste.

Another aspect of this invention is a supplement especially designed for a show animal which comprises *Stevia* extract, steviol, or steviol precursor. The animal should be fed this supplement daily for at least one month, and preferably for at least two months prior to the competition in order for its skin to be at its optimal tan condition. In preferred embodiments, the supplement is in the form of a treat or chew.

Preferred Oral Compositions

Food products or foodstuffs are, for example, beverages such as non-alcoholic and alcoholic drinks as well as liquid preparations to be added to drinking water and liquid food. Non-alcoholic drinks are for instance: soft drinks, sport drinks, fruit juices, (e.g. orange juice, apple juice and grapefruit juice); lemonades, teas, near-water drinks, milk and other dairy drinks (e.g. yoghurt drinks) and diet drinks. In another embodiment, food products or foodstuffs refer to solid or semi-solid foods comprising the composition according to the invention. These forms can include, but are not limited to, baked goods such as: cakes and cookies, puddings, dairy products, confections, snack foods, or frozen confections or novelties (e.g. ice cream, milk shakes), prepared frozen meals, candy, snack products (e.g. potato crisps/chips), liquid food such as soups, spreads, sauces, salad dressings, prepared meat products, cheese, yogurt and any other fat- or oil-containing foods, and food ingredients (e.g. wheat flour). The food product may be a prepared and packaged food (e.g. mayonnaise, salad dressing, bread, or cheese food).

Dietary supplements of the present invention are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a tablet or capsule and most preferably in the form of a hard (shell) gelatine capsule. Suitable excipients and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation and administration may be found in the latest edition of *Remington's Pharmaceutical Sciences* (Maack Publishing Co., Easton, Pa.).

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food, e.g. enclosed in caps of food or beverage containers for release immediately before consumption. The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavourings, inert ingredients, and the like.

In some embodiments, the dietary supplements further comprise vitamins and minerals including, but not limited to, calcium phosphate or acetate, tribasic; potassium phosphate, dibasic; magnesium sulphate or oxide; salt (sodium chloride); potassium chloride or acetate; ascorbic acid; ferric orthophosphate; niacinamide; zinc sulphate or oxide; calcium pantothenate; copper gluconate; riboflavin; beta-carotene; pyridoxine hydrochloride; thiamine mononitrate; folic acid; biotin; chromium chloride or picolonate; potassium iodide; sodium selenate; sodium molybdate; phylloquinone; vitamin D3; cyanocobalamin; sodium selenite; copper sulphate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g. energy bars or meal replacement bars or beverages) comprising the composition according to the invention. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g. sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk, soy protein, soy protein isolate, caseinate (e.g. sodium caseinate, sodium calcium caseinate, calcium caseinate, potassium caseinate), animal and vegetable protein and hydrolysates or mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See *Modern Nutrition in Health and Disease*, Eighth Edition, Lea & Febiger, publishers, 1986, especially Volume 1, pages 30-32.

The nutritional supplement can also contain other ingredients, such as one or a combination of other vitamins, minerals, antioxidants, fibers and other dietary supplements (e.g. protein, amino acids, choline, lecithin, omega-3 fatty acids). Selection of one or several of these ingredients is a matter of formulation, design, consumer and end-user preference. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulphate or oxide; salt (sodium chloride); potassium chloride or acetate; ascorbic acid; ferric orthophosphate; niacinamide; zinc sulphate or oxide; calcium pantothenate; copper gluconate; riboflavin; beta-carotene; pyridoxine hydrochloride; thiamine mononitrate; folic acid; biotin; chromium chloride or picolonate; potassium iodide; sodium selenate; sodium molybdate; phylloquinone; vitamin D3; cyanocobalamin; sodium selenite; copper sulphate; vitamin A; vitamin C; Vitamin E, inositol; and potassium iodide. Moreover, a multi-vitamin and mineral supplement may be added to the nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

It is understood by those of skill in the art that other ingredients can be added to those described herein, for example, fillers, emulsifiers, preservatives, etc. for the processing or manufacture of a nutritional supplement.

Additionally, flavors, coloring agents, spices, nuts and the like may be incorporated into the nutraceutical composition. Flavourings can be in the form of flavored extracts, volatile oils, chocolate flavourings, peanut butter flavoring, cookie crumbs, crisp rice, vanilla or any commercially available flavoring. Examples of useful flavourings include, but are not limited to: pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as lemon oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the nutraceutical compositions. Examples of suitable emulsifiers include, but are not limited to, lecithin (e.g. from egg or soy), and/or mono- and di-glycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutraceutical composition can contain natural or artificial (preferably low calorie) sweeteners, such as, but not limited to: saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycaemia.

Dosages

For human use, the recommended dosage for *Stevia* extract is in the range of 0.1 to 500 g/kg body weight per day; preferably from 0.5 to 250 mg/kg body weight per day; and more preferably from 1.0 to 50 mg/kg body weight per day.

For steviol, the preferred dosages range from 0.01 to 100 mg/kg body weight per day, preferably 0.1 to 50 mg/kg body weight per day, and more preferably from 0.5 to 25 mg/kg body weight per day, and/or 0.5 to 10 mg/kg body weight per day.

For steviol precursors, the preferred dosages range from 0.05 to 1000 mg/kg body weight per day, preferably from 0.5 to 500 mg/kg body weight per day; and more preferably from 1.0 to 100 mg/kg body weight per day.

The preferred daily dosage of the subject composition as specified above may be administered in the form of one or more dosage units such as, e.g., a tablet. Most preferably the daily dosage of the subject composition is provided in the form of one dosage unit taken twice daily, for a total of two dosage units a day, or in the form of two dosage units taken twice daily, for a total of four dosage units a day. Compared to taking the total daily dose once a day, twice daily dosing of half the total daily dose in one or more dosage units per dose provides improved absorption and better maintenance of blood levels of the essential ingredients. For *Stevia* extract or precursors of steviol, the dosage per dosage unit ranges from 30-1000 mg; for steviol it ranges from 10 to 500 mg.

For human use, the recommended dosage for steviol glycosides is in the range of 0.05 mg per kg body weight to about 100 mg per kg body weight per day. More preferred is a daily dosage of about 0.1 to about 20 mg per kg body weight, and especially preferred is a daily dosage of about 1.0 to 10.0 mg per kg body weight.

Recommended Levels in Foodstuffs

| Food Category | Steviol precursor (steviol glycoside, e.g. Rebaudioside A or stevioside) mg/kg food | Steviol precursor (steviol glycoside) mg per dose | Free steviol mg/kg food | Free steviol per mg dose |
|---|---|---|---|---|
| Cereals (oatmeal, cold cereal, cereal bars) | 50-1000 | 2-40/40 g | 250-750 | 10-30/40 g |
| Ready-to-drink teas | 20-480 | 5-120/0.25 L | 20-200 | 5-50/0.25 L |
| Fruit juice drinks | 50-600 | 12.5-150/0.25 L | 30-200 | 5-100/0.25 L |
| Diet soft drinks | 50-600 | 12.5-150/0.25 L | 30-200 | 5-50/0.25 L |
| Energy drinks | 50-600 | 12.5-150/0.25 L | 120-600 | 30-150/0.25 L |
| Flavored waters | 20-400 | 5-100/0.25 L | 20-1200 | 5-30/0.25 L |
| Fine bakery products | 50-1000 | 2-40/40 g | 250-750 | 10-30/40 g |
| Confectionary, candy | 1000-6000 | 20-120/20 g | | 5-20/20 g |

In a preferred embodiment, the *Stevia* extract- or steviol- or steviol-precursor-containing nutraceutical composition is eaten on a regular basis, i.e. at least daily for a sustained period of time (i.e. at least one week, preferably at least two weeks, and more preferably for at least three weeks, or at least one or two months) until the skin tan enhancement is noted. After this time, the consumer may choose to lessen the dosage.

In a further embodiment the invention relates to the use of steviol, a steviol precursor, such as a steviol glycoside, or a *Stevia* extract for stimulating the melanin formation in human epidermal melanocytes The following non-limiting examples are presented to better illustrate the invention.

EXAMPLE 1

Induction of Melanin Synthesis by Steviol in Human Epidermal Melanocytes

Quantification of Melanin Synthesis in Cell Culture:

Normal human melanocytes NHM (HEMn-MP, Clonetics) were seeded in 96 well cell culture plates and grown to subconfluence for two days in a mixture of M2-Medium (Clonetics) and Medium (Promocell). Culture medium was exchanged with Culture Medium containing Steviol (96%) and melanogenesis progressed for another three days at 37° C. with another medium exchange on day two. Including cell layer and culture supernatant the total melanin was extracted using 1.7M KOH with vigorous shaking at RT. The total melanin content was determined at 405 nm in an absorbance plate reader versus a control (100%)

The results are summarized in the table below:

| | Positive control Glycyrrhizin | Steviol | | |
|---|---|---|---|---|
| Control | 1.5 mM | 0.25 microM | 0.5 micro M | 1 micro M |
| 100% | 132% | 109% | 124% | 130% |

Glycyrrhizin is used as a positive control since it is a known inducer of melanogenesis. Steviol shows a clear dose dependent positive effect on the production of melanin in human melanocytes. Furthermore, as can be retrieved from the results, steviol is about 1000 times more potent than the positive control Glycyrrhizin.

EXAMPLE 2

Tablet

| | |
|---|---|
| Steviol | 150 mg |
| Microcrystalline cellulose | 300 mg |
| Lactose | 300 mg |
| Crospovidone | 10 mg |
| Mg-Stearate | 2.5 mg |
| $SiO_2$ | 2.5 mg |

Steviol, microcrystalline cellulose, and $SiO_2$ are mixed in a tumbler mixer for 10 min. Then, lactose is added and the composition is mixed for a further 10 min. Crospovidone is combined with the other ingredients and mixed for 10 min. Finally, Mg-stearate is added to the other components and mixed for another 2 min. The mixture is compressed to tablets. One tablet per day is taken in the morning with breakfast.

EXAMPLE 3

Preparation of a Hard Gelatine Capsule

| Ingredient | Amount per Capsule |
|---|---|
| Steviol | 100 mg |
| Lactose | 295 mg |
| $SiO_2$ | 5 mg |

Steviol, lactose and $SiO_2$ are mixed in a tumbler mixer for 15 minutes and then filled into capsules.

Two capsules per day for 3 months may be administered to a human adult for increasing the skin tan. The dose can be increased on demand to up to 3 capsules per day. To support skin tanning on a regular basis 1 capsule can be taken on a regular basis.

EXAMPLE 4

Preparation of an Instant Flavored Soft Drink

| Ingredient | Amount [g] |
| --- | --- |
| Steviol | 0.5 |
| Sucrose, fine powder | 763.1 |
| Ascorbic acid, fine powder | 2.0 |
| Citric acid anhydrous powder | 55.0 |
| Lemon flavor | 8.0 |
| Trisodium citrate anhydrous powder | 6.0 |
| Tricalciumphosphate | 5.0 |
| beta-Carotene 1% CWS from DNP AG, Kaiseraugst, Switzerland | 0.4 |
| Total amount | 840 |

All ingredients are blended and sieved through a 500 μm sieve. The resulting powder is put in an appropriate container and mixed in a tubular blender for at least 20 minutes. For preparing the drink, 105 g of the obtained mixed powder are mixed with sufficient water to produce one liter of beverage.

The ready-to-drink soft drink contains ca. 15 mg enriched steviol extract per serving (250 ml). As a regular skin tanning supporting drink, 2 servings per day (500 ml) may be drunk.

EXAMPLE 5

Preparation of a Fortified Non-Baked Cereal Bar

| Ingredient | Amount [g] |
| --- | --- |
| Steviol | 0.3 |
| Water | 54.0 |
| Salt | 1.5 |
| Glucose syrup | 130.0 |
| Invert sugar syrup | 95.0 |
| Sorbitol Syrup | 35.0 |
| Palm kernel fat | 60.0 |
| Baking fat | 40.0 |
| Lecithin | 1.7 |
| Hardened palm-oil | 2.5 |
| Dried and cut apple | 63.0 |
| Cornflakes | 100.0 |
| Rice crispies | 120.0 |
| Wheat crispies | 90.0 |
| Roasted hazelnut | 40.0 |
| Skimmed milk powder | 45.0 |
| Apple flavor 74863-33 | 2.0 |
| Citric acid | 5.0 |
| Total amount | 885 |

The enriched steviol is premixed with skimmed milk powder and placed in a planetary bowl mixer. Cornflakes and rice crispies are added and the total is mixed gently. Then the dried and cut apples are added. In one cooking pot, water and salt are mixed in the amounts given above (solution 1). In a second cooking pot, glucose-, invert sugar- and sorbitol-syrups are mixed in the amounts given above (solution 2). The fat phase constitutes a mixture of baking fat, palm kernel fat, lecithin and emulsifier. Solution 1 is heated to 110° C. Solution 2 is heated to 113° C. and then cooled in a cold water bath. Subsequently, solutions 1 and 2 are combined. The fat phase is melted at 75° C. in a water bath, then added to the combined mixture of solutions 1 and 2. Apple flavor and citric acid are added to the liquid sugar/fat mix. The liquid mass is added to the dry ingredients and mixed well in the planetary bowl mixer. The mass is put on a marble plate and rolled to the desired thickness. The mass is cooled down to room temperature and cut into pieces. The non-baked cereal bar contains ca. 10 mg steviol per serving (30 g). To support a natural skin tan, 1-2 cereal bars may be eaten per day.

The invention claimed is:

1. A method of enhancing tanned skin in a human in need thereof by increasing melanin formation in epidermal melanocytes, wherein the method comprises orally administering to a human in need of increased melanin formation in epidermal melanocytes a composition comprising steviol and an effective amount of at least one additional ingredient selected from the group consisting of: lutein, lycopene, astaxanthin, zeaxanthin, β-carotene, canthaxanthin, L-tyrosine, vitamin E, vitamin D, copper, green tea extract, lipoic acid, and selenomethionine, wherein the composition is administered daily for at least two weeks, and wherein the steviol is administered in an amount from 0.01 to 100 mg/kg body weight per day.

2. The method of claim 1, wherein the composition is a nutraceutical composition and further comprises a nutraceutically acceptable carrier.

3. The method of claim 1, wherein the at least one additional ingredients is selected from the group consisting of: lutein, lycopene, β-carotene, canthaxanthin, L-tyrosine, vitamin E, vitamin D and copper.

4. The method of claim 1, wherein the effective amount of the additional ingredient is 5-250 mg/kg per day.

5. The method of claim 1, wherein the steviol is administered in an amount from 0.5 to 25 mg/kg body weight per day.

* * * * *